United States Patent
Cho et al.

(10) Patent No.: US 7,094,913 B2
(45) Date of Patent: Aug. 22, 2006

(54) SYNTHESIS OF 7-MEMBERED CARBOCYCLIC COMPOUND HAVING DIEXOMETHYLENE GROUPS

(75) Inventors: Yong Seo Cho, Seoul (KR); Moon Ho Chang, Seoul (KR); Hun Yeong Koh, Seoul (KR); Ae Nim Pae, Seoul (KR); Hyun Jung Kang, Seoul (KR)

(73) Assignee: Korea Institute of Science and Technology, (KR)

( * ) Notice: Subject to any disclaimer, the term of this patent is extended or adjusted under 35 U.S.C. 154(b) by 141 days.

(21) Appl. No.: 10/823,707

(22) Filed: Apr. 14, 2004

(65) Prior Publication Data

US 2005/0059832 A1    Mar. 17, 2005

(30) Foreign Application Priority Data

Sep. 17, 2003    (KR)   .................... 10-2003-0064383

(51) Int. Cl.
*C07D 313/04*    (2006.01)

(52) U.S. Cl. ........................................ 549/346

(58) Field of Classification Search ................ 549/346
See application file for complete search history.

(56) References Cited

OTHER PUBLICATIONS

Article "The 91st National Meeting of the Korean Chemical Society", ISSN 1229-6708, Apr. 18-19, 2003, p. 363.
Fernando Lopez, et al., "Atom-Efficient Assembly of 1,5-Oxygen-Bridged Medium-Sized Carbocycles by Sequential Combination of a Ru-Catalyzed Alkyne-Alkene Coupling and a Prins-Type Cyclization", J. Am. Chem. Soc. 2002 American Chemical Society, pp. 4218-4219.
Fouzia Machrouhi, "Sequenced Reactions with Samarium(II) Iodide. A Complementary Annulation Process Providing Access to Seven-, Eight-, and Nine-Membered Carbocycles", J. Org. Chem. 1999 American Chemical Society, pp. 4119-4123.
Gary A. Molander, et al., "Neighboring Group Participation in Lewis Acid-Promoted [3+4] and [3+5] Annulations. The Stereocontrolled Synthesis of Tricylic Ethers", J. Org. Chem. 1993, American Chemical Society, pp. 5931-3427.
Dale L. Boger, et al., "Thermal, Four-Carbon + Three-Carbon Cycloaddition Reaction of Cyclopropenone Ketals. Total Synthesis of Deacetamidocolchiceine: Formal Total Synthesis of Colchicine", J. Org. Chem. 1985 American Chemical Society, pp. 3425-3427.
English Translation of I31P121 on Abstract of The 91st National Meeting of the Korean Chemical Society Program and Abstracts.

*Primary Examiner*—Taofiq Solola
(74) *Attorney, Agent, or Firm*—Merchant & Gould, P.C.; William E. Beaumont

(57) ABSTRACT

The present invention relates to a synthesis of a 7-membered carbocyclic compound having diexomethylene groups, more particularly to a synthesis of a 7-membered carbocyclic compound having diexomethylene groups, a novel compound having the structure represented by the following Chemical Formula 1, from trimethylsilanylmethyl-allenol derivative by the intramolecular Prins cyclization using Lewis acid. The 7-membered carbocyclic compound is a useful intermediate for synthesis of other multicyclic compounds.

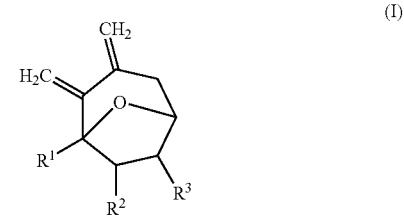

(I)

In Chemical Formula 1, $R^1$ is a $C_1$ to $C_6$ alkyl group, and $R^2$ and $R^3$ is respectively a hydrogen atom, or $R^1$, $R^2$ and $R^3$ may be connected with neighboring substituents to form a 5 to 10-membered aliphatic or aromatic ring.

31 Claims, No Drawings

US 7,094,913 B2

SYNTHESIS OF 7-MEMBERED CARBOCYCLIC COMPOUND HAVING DIEXOMETHYLENE GROUPS

BACKGROUND OF THE INVENTION

1. Field of the Invention

The present invention relates to a synthesis of a 7-membered carbocarbocyclic compound having diexomethylene groups, more particularly to a synthesis of a 7-membered carbocyclic compound having diexomethylene groups, a novel compound having the structure represented by the following Chemical Formula 1, from trimethylsilanylmethyl-allenol derivative by the intramolecular Prins cyclization using Lewis acid. The 7-membered cyclic compound is a useful intermediate for synthesis of other multicyclic compounds.

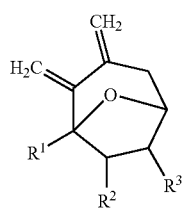
(I)

In Chemical Formula 1, $R^1$ is a $C_1$ to $C_6$ alkyl group, and $R^2$ and $R^3$ is respectively a hydrogen atom, or $R^1$, $R^2$ and $R^3$ may be connected with neighboring substituents to form a 5 to 10-membered aliphatic or aromatic ring.

2. Description of the Related Art 7-membered carbocyclic compounds are important ingredients of biologically active natural substances and medicines. Recently, they are gaining interest in genetics because they are known to take part in cell division. For example, colchicine, which is known to be effective in treating gout [J. Org. Chem. 1985, 50, 3425–3427], is a tricyclic compound having a 7-membered ring. According to a recent report, colchicine derivatives have high cell toxicity against general cancer cells and their resistant MDRs.

Since 7-membered carbocyclic compounds have good biological activity, development of a 7-membered carbocyclic compound with a new structure is a prerequisite for drug researches.

A cyclic compound having diexomethylene groups can be expanded to other multicyclic compounds through Diels-Alder reactions. Therefore, the compound represented by Chemical Formula 1, which has diexomethylene groups, is a very useful intermediate in synthesizing a multicyclic compound via Diels-Alder reactions.

SUMMARY OF THE INVENTION

It is an object of the present invention to provide a 7-membered carbocyclic compound having diexomethylene groups, which is represented by Chemical Formula.

It is another object of the present invention to provide a method for synthesizing the novel compound represented by Chemical Formula 1 from a trimethylsilanylmethyl-allenol derivative by the intramolecular Prins cyclization using Lewis acid.

DETAILED DESCRIPTION OF THE PREFERRED EMBODIMENTS

The present invention is characterized by a 7-membered carbocyclic compound having a new structure, which is represented by the following Chemical Formula 1:

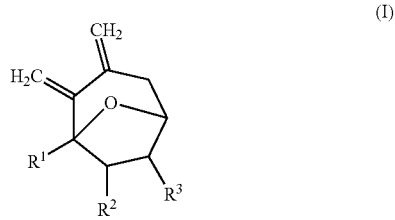
(I)

In Chemical Formula 1, $R^1$ is a $C_1$ to $C_6$ alkyl group, and $R^2$ and $R^3$ is respectively a hydrogen atom, or $R^1$, $R^2$ and $R^3$ may be connected with neighboring substituents to form a 5 to 10-membered aliphatic or aromatic ring.

Also, the present invention is characterized by a method of synthesizing the compound represented by Chemical Formula 1 from a trimethylsilanylmethyl-allenol derivative by the intramolecular Prins cyclization in the presence of Lewis acid.

Hereinafter, the present invention is described in more detail.

The 7-membered carbocyclic compound represented by Chemical Formula 1, which is provided by the present invention, is a novel compound having diexomethylene groups, and it can be used as an active ingredient of medicines, or intermediate of synthesizing multicyclic compounds in the field of medicine and precise chemistry.

Specific examples of the compound provided by the present invention include:

a compound wherein $R^1$ is a $C_1$ to $C_3$ alkyl group, and $R^2$ and $R^3$ is respectively a hydrogen atom;

a compound wherein $R^1$ and $R^2$ are connected with each other to form a 5 to 10-membered aliphatic or aromatic ring, and $R^3$ is a hydrogen atom; and a compound wherein $R^2$ and $R^3$ are connected with each other to form a 5 to 10-membered aliphatic or aromatic ring, and $R^1$ is a hydrogen atom.

The present invention also provides a method of synthesizing the compound represented by Chemical Formula 1 from a trimethylsilanylmethyl-allenol derivative by the intramolecular Prins cyclization in the presence of Lewis acid.

For the Lewis acid, such common Lewis acids as trimethylsilyl trifluoromethanesulfonate (TMSOTf) or indium halide ($InX_3$, X=Cl or Br) can be used. Most preferably, TMSOTf is used. Preferably, the Lewis acid is used in 1.0 to 1.5 equivalent of the starting material, a trimethylsilanylmethyl-allenol derivative. For the reaction solvent, common organic solvents such as diethyl ether, tetrahydrofuran, dichloromethane, chloroform and ethyl acetate can be used. Most preferably, diethyl ether is used. The reaction is performed at from −90° C. to room temperature (25° C.) for about 3 to 5 hours.

Since the aforementioned intramolecular Prins cyclization is industrially very probable because it is relatively simple and offers good yield.

The compound represented by Chemical Formula 1 is useful in the field of medicine and precise chemistry. Because the compound represented by Chemical Formula 1 has diexomethylene groups, other multicyclic compounds can be prepared from it by Diels-Alder reactions.

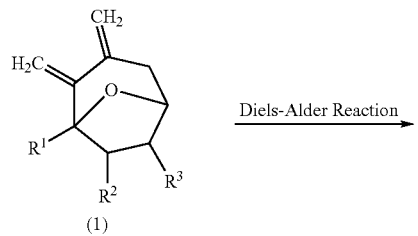

(1)

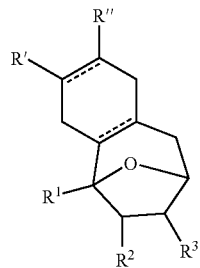

Hereinafter, the present invention is described in more detail through Examples. However, the following Examples should not be construed as limiting the scope of the present invention.

EXAMPLES

Example 1

Synthesis of 1-methyl-2,3-dimethylene-8-oxa-bicyclo[3.2.1]octane

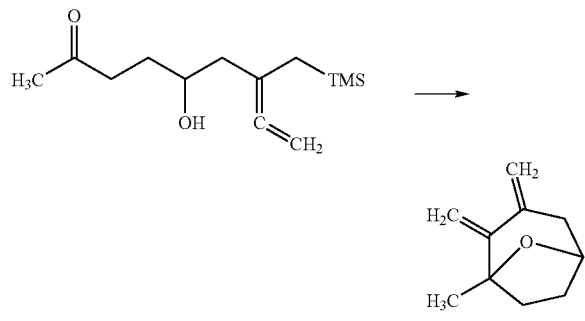

1.50 mL of diethyl ether was added to 5-hydroxy-7-trimethylsilanylmethyl-nona-7,8-diene-2-one (86 mg, 0.36 mmol) under nitrogen atmosphere. While stirring at −78° C., trimethylsilyl trifluoromethanesulfonate (TMSOTf; 64.7 μL, 0.36 mmol) was added. While stirring the reaction mixture, the reaction temperature was slowly increased to room temperature for 3 hours. The reaction mixture was stirred at room temperature for 30 minutes. After the reaction was completed, H$_2$O was added. After stirring for about 5 minutes, the reaction mixture was diluted with ethyl acetate (EtOAc) and washed with water and saturated brine. The organic layer was separated from the reaction mixture and dried with anhydrous magnesium sulfate (MgSO$_4$). The solvent was removed under reduced pressure and the remaining material was purified with column chromatography (EtOAc/n-hexane=1/5) to obtain 51 mg of the product (94%).

$^1$H NMR (300 MHz, CDCl$_3$) δ 5.17 (s, 1H), 5.29 (s, 1H), 4.78 (t, 2H, J=5.6 Hz), 4.53 (s, 1H), 2.69 (d, 1H, J=12.1 Hz), 2.36 (m, 2H), 1.85 (m, 3H), 1.51 (s, 3H); $^{13}$C NMR (75 MHz, CDCl$_3$) δ 152.51, 143.41, 112.19, 104.33, 81.86, 76.23, 42.42, 37.47, 30.22, 22.87 ppm.

Example 2

Synthesis of 2,3-dimethylene-1-phenyl-8-oxa-bicyclo[3.2.1]octane

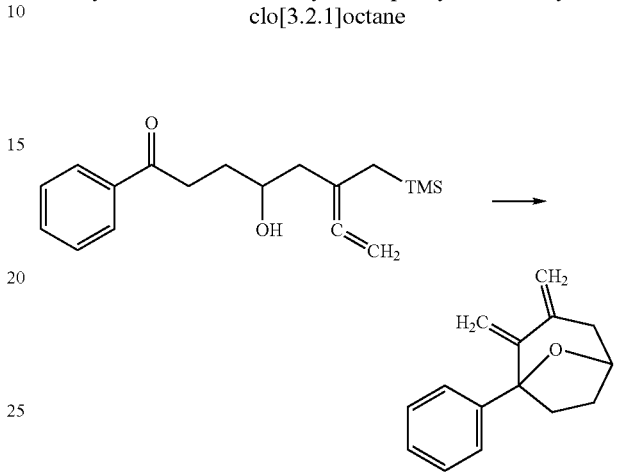

1.50 mL of diethyl ether was added to 4-hydroxy-1-phenyl-6-trimethylsilanylmethyl-octa-6,7-diene-1-one (110 mg, 0.36 mmol) under nitrogen atmosphere. While stirring at −78° C., TMSOTf (64.7 μL, 0.36 mmol) was added. While stirring the reaction mixture, the reaction temperature was slowly increased to room temperature for 3 hours. The reaction mixture was stirred at room temperature for 30 minutes. After the reaction was completed, H$_2$O was added. After stirring for about 5 minutes, the reaction mixture was diluted with EtOAc and washed with water and saturated brine. The organic layer was separated from the reaction mixture and dried with anhydrous MgSO$_4$. The solvent was removed under reduced pressure and the remaining material was purified with column chromatography (EtOAc/n-hexane=1/5) to obtain 74 mg of the product (96%).

$^1$H NMR (300 MHz, CDCl$_3$) δ 7.33 (m, 5H), 5.20 (s, 1H), 4.94 (s, 1H), 4.87 (s, 1H), 4.74 (s, 1H), 3.99 (s, 1H), 2.84 (d, 1H, J=17 Hz), 2.39 (t, 1H, J=7.9 Hz), 2.29 (d, 1H, J=14.2 Hz), 2.17 (m, 2H), 1.92 (m, 1H); $^{13}$C NMR (75 MHz, CDCl$_3$) δ 153.75, 143.58, 143.10, 128.06, 127.27, 127.00, 112.46, 108.18, 86.98, 76.04, 42.55, 37.17, 29.73 ppm.

Example 3

Synthesis of 9,10-dimethylene-12-oxa-tricyclo[6.3.1.0$^{2,7}$]dodeca-2,3,5-triene

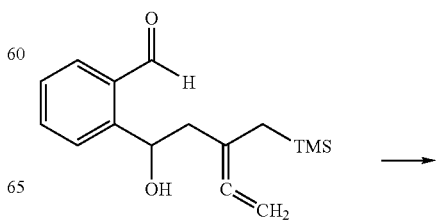

-continued

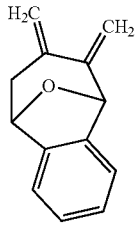

5.2 mL of diethyl ether was added to 2-(1-hydroxy-3-trimethylsilanylmethyl-penta-3,4-dienyl)-benzaldehyde (358 mg, 1.30 mmol) under nitrogen atmosphere. While stirring at −78° C., TMSOTf (235 μL, 1.30 mmol) was added. While stirring the reaction mixture, the reaction temperature was slowly increased to room temperature for 3 hours. The reaction mixture was stirred at room temperature for 30 minutes. After the reaction was completed, $H_2O$ was added. After stirring for about 5 minutes, the reaction mixture was diluted with EtOAc and washed with water and saturated brine. The organic layer was separated from the reaction mixture and dried with anhydrous $MgSO_4$. The solvent was removed under reduced pressure and the remaining material was purified with column chromatography (EtOAc/n-hexane=1/6) to obtain 185 mg of the product (77%).

$^1$H NMR (300 MHz, $CDCl_3$) δ 7.24 (m, 4H), 5.40 (s, 1H), 5.35 (d, 1H, J=4.8 Hz), 5.15 (s, 1H), 5.11 (s, 1H), 4.97 (s, 1H), 4.67 (s, 1H), 3.02 (br d, 1H, J=15.0 Hz), 2.37 (d, 1H, J=14.4 Hz); $^{13}$C NMR (75 MHz, $CDCl_3$) δ 146.20, 143.56, 143.01, 139.90, 127.68, 120.68, 114.16, 107.22, 83.31, 79.10, 38.56 ppm.

Example 4

Synthesis of 9,10-dimethylene-11-oxa-tricyclo[5.3.1.0$^{1,5}$]undecane

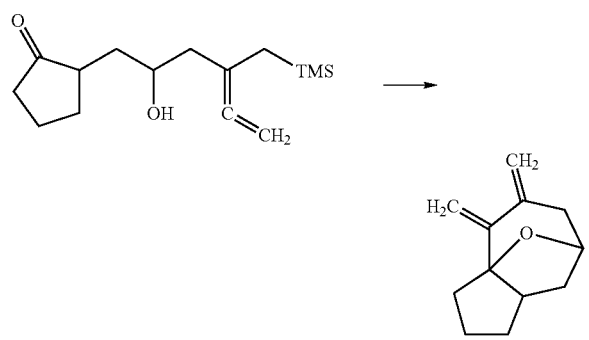

1.1 mL of diethyl ether was added to 2-(2-hydroxy-4-trimethylsilanylmethyl-hexa-4,5-dienyl)-cyclopentanone (70 mg, 0.26 mmol) under nitrogen atmosphere. While stirring at −78° C., TMSOTf (48 μL, 0.26 mmol) was added. While stirring the reaction mixture, the reaction temperature was slowly increased to room temperature for 3 hours. The reaction mixture was stirred at room temperature for 30 minutes. After the reaction was completed, $H_2O$ was added. After stirring for about 5 minutes, the reaction mixture was diluted with EtOAc and washed with water and saturated brine. The organic layer was separated from the reaction mixture and dried with anhydrous $MgSO_4$. The solvent was removed under reduced pressure and the remaining material was purified with column chromatography (EtOAc/n-hexane=1/15) to obtain 36 mg of the product (77%).

$^1$H NMR (300 MHz, $CDCl_3$) δ 5.17 (s, 1H), 5.04 (s, 1H), 4.81 (s, 2H), 4.58 (t, 1H, J=6.3 Hz), 2.73 (dd, 1H, $J_1$=14.6 Hz, $J_2$=2.4 Hz), 2.35 (m, 1H), 2.17 (m, 2H), 1.81 (m, 6H), 1.38 (m, 1H); $^{13}$C NMR (75 MHz, $CDCl_3$) δ 150.59, 144.25, 111.22, 103.66, 94.02, 77.70, 47.06, 41.53, 40.88, 34.60, 32.77, 25.02 ppm.

Example 5

Synthesis of 10,11-dimethylene-12-oxa-tricyclo[6.3.1.0$^{1,6}$]dodecane

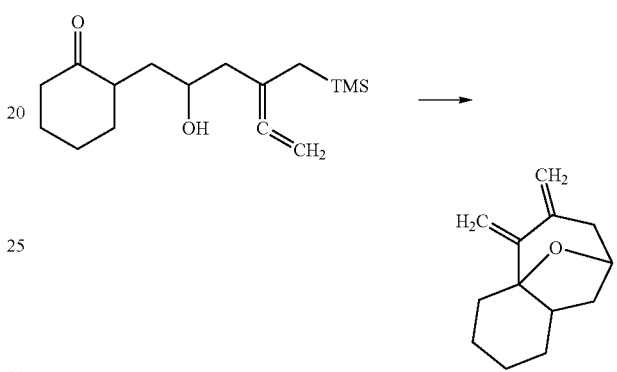

1.5 mL of diethyl ether was added to 2-(2-hydroxy-4-trimethylsilanylmethyl-hexa-4,5-dienyl)-cyclohexanone (100 mg, 0.36 mmol) under nitrogen atmosphere. While stirring at −78° C., TMSOTf (64.5 μL, 0.36 mmol) was added. While stirring the reaction mixture, the reaction temperature was slowly increased to room temperature for 3 hours. The reaction mixture was stirred at room temperature for 30 minutes. After the reaction was completed, $H_2O$ was added. After stirring for about 5 minutes, the reaction mixture was diluted with EtOAc and washed with water and saturated brine. The organic layer was separated from the reaction mixture and dried with anhydrous $MgSO_4$. The solvent was removed under reduced pressure and the remaining material was purified with column chromatography (EtOAc/n-hexane=1/6) to obtain 53 mg of the product (78%).

$^1$H NMR (300 MHz, $CDCl_3$) δ 5.20 (s, 1H), 5.12 (s, 1H), 4.79 (s, 1H), 4.74 (s, 1H), 4.51 (s, 1H), 2.70 (d, 1H, J=13.7 Hz), 2.15 (d, 1H, J=14.3 Hz), 1.96 (m, 4H), 1.65 (m, 5H), 1.22 (m, 2H); $^{13}$C NMR (75 MHz, $CDCl_3$) δ 153.22, 143.83, 112.17, 106.14, 82.65, 73.73, 43.35, 42.09, 38.11, 31.43, 29.61, 23.21, 20.54 ppm.

Example 6

Synthesis of 11,12-dimethylene-13-oxa-tricyclo[7.3.1.0$^{1,7}$]tridecane

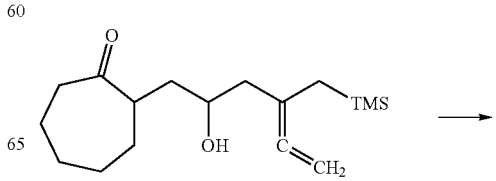

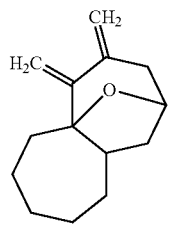

1.30 mL of ether was added to 2-(2-hydroxy-4-trimethylsilanylmethyl-hexa-4,5-dienyl)-cycloheptanone (95 mg, 0.32 mmol) under nitrogen atmosphere. While stirring at −78° C., TMSOTf (58.4 μL, 0.32 mmol) was added. While stirring the reaction mixture, the reaction temperature was slowly increased to room temperature for 3 hours. The reaction mixture was stirred at room temperature for 30 minutes. After the reaction was completed, $H_2O$ was added. After stirring for about 5 minutes, the reaction mixture was diluted with EtOAc and washed with water and saturated brine. The organic layer was separated from the reaction mixture and dried with anhydrous $MgSO_4$. The solvent was removed under reduced pressure and the remaining material was purified with column chromatography (EtOAc/n-hexane=1/6) to obtain 59 mg of the product (90%).

$^1$H NMR (600 MHz, $CDCl_3$) δ 5.18 (s, 1H), 5.10 (s, 1H), 4.7 6(s, 1H), 4.49 (s, 1H), 2.69 (s, 1H, J=14.2 Hz), 2.14 (d, 1H, J=14.4 Hz), 1.90 (m, 5H), 1.54 (m, 4H), 1.50 (m, 2H), 1.18 (m, 2H); $^{13}$C NMR (75 MHz, $CDCl_3$) δ 153.59, 144.90, 111.98, 105.15, 86.91, 75.53, 47.81, 42.55, 40.41, 34.63, 34.00, 31.98, 29.72, 25.08 ppm.

Comparative Example

Diels-Alder Reaction using 9,10-dimethylene-12-oxa-tricyclo[6.3.1.0$^{2,7}$]dodeca-2,3,5-triene The following is an example of synthesizing another multicyclic compound by Diels-Alder from the compound represented by Chemical Formula 1.

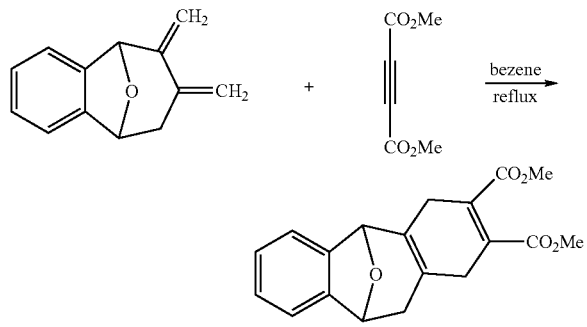

2.0 mL of benzene was added to 9,10-dimethylene-12-oxa-tricyclo[6.3.1.0$^{2,7}$]dodeca-2,3,5-triene (37 mg, 0.2 mmol) under nitrogen atmosphere. After adding dimethylacetylene dicarboxylate (85.62 mg, 0.6 mmol), the reaction mixture was stirred with reflux at 85° C. for 5 hours. After the reaction was completed, $H_2O$ was added. After stirring for about 5 minutes, the reaction mixture was diluted with ethyl acetate and washed with water and saturated brine. The organic layer was separated from the reaction mixture and dried with anhydrous $MgSO_4$. The solvent was removed under reduced pressure and the remaining material was purified with column chromatography (EtOAc/n-hexane=1/6) to obtain 39 mg of the product (60%).

$^1$H NMR (300 MHz, $CDCl_3$) δ 7.17 (m, 4H), 5.42 (d, 1H, J=5.97 Hz), 4.92 (s, 1H), 3.77 (s, 1H), 3.73 (s, 1H), 2.84 (m, 6H); $^{13}$C NMR (75 MHz, $CDCl_3$) δ 168.7, 147.7, 142.9, 133.6, 131.2, 130.4, 128.2, 127.4, 127.3, 121.4, 119.7, 117.8, 79.9, 78.8, 52.7, 32.9, 32.4, 28.9 ppm.

As described above, the present invention offers the following advantages:

1) Dimethylene cyclic compounds having a variety of structures can be synthesized using trimethylsilanylmethylalenol derivative as a starting material.

2) The synthesis reaction is simple.

3) The synthesis yield is high.

4) The diexomethylene cyclic compound is useful as an intermediate of synthesizing multicyclic compounds having a 7-membered ring, which are very important in the field of precise chemistry, by Diels-Alder reactions.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A 7-membered carbocyclic compound with diexomethylene groups having the formula (I):

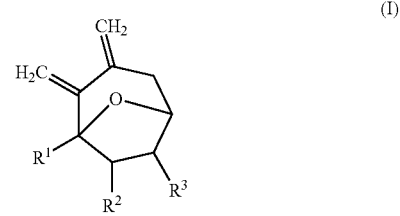

wherein $R^1$ is a hydrogen atom, a $C_1$ to $C_6$ alkyl group or a phenyl group, and $R^2$ and $R^3$ is each a hydrogen atom, or $R^1$, $R^2$ and $R^3$ are connected with neighboring substituents to form a 5 to 10-membered aliphatic or aromatic ring.

2. The compound of claim 1, wherein $R^1$ is $C_1$ to $C_3$ alkyl, and each of $R^2$ and $R^3$ is a hydrogen atom.

3. The compound of claim 1, wherein $R^1$ and $R^2$ are connected with each other to form a 5 to 10-membered aliphatic or aromatic ring, and $R^3$ is a hydrogen atom.

4. The compound of claim 1, wherein $R^2$ and $R^3$ are connected with each other to form a 5 to 10-membered aliphatic or aromatic ring, and $R^1$ is a hydrogen atom.

5. The compound of claim 2, wherein $R^1$ is methyl.

6. The compound of claim 1, wherein $R^1$ is phenyl, and each of $R^2$ and $R^3$ are hydrogen.

7. The compound of claim 4, wherein $R^2$ and $R^3$ are connected with each other to form a phenyl group.

8. The compound of claim 3, wherein $R^1$ and $R^2$ are connected with each other to form a cyclopentyl group.

9. The compound of claim 3, wherein $R^1$ and $R^2$ are connected with each other to form a cyclohexyl group.

10. The compound of claim 3, herein $R^1$ and $R^2$ are connected with each other to form a cycloheptyl group.

11. The compound of claim 1, which is 1-methyl-2,3-dimethylene-8-oxa-bicyclo[3.2.1]octane.

12. The compound of claim 1, which is 2,3-dimethylene-1-phenyl-8-oxa-bicyclo[3.2.1]octane.

13. The compound of claim 1, which is 9,10-dimethylene-12-oxa-tricyclo[6.3.1.0$^{2,7}$]dodeca-2,3,5-triene.

14. The compound of claim 1, which is 9,10-dimethylene-11-oxa-tricyclo[5.3.1.0$^{1,5}$]undecane.

15. The compound of claim 1, which is 10,11-dimethylene-12-oxa-tricyclo[6.3.1.0$^{1,6}$]dodecane.

16. The compound of claim 1, which is 11,12-dimethylene-13-oxa-tricyclo[7.3.1.0$^{1,7}$]tridecane.

17. A method of synthesizing a 7-membered carbocyclic compound with diexomethylene groups, and having the formula (I), which comprises reacting a trimethylsilanylmethyl-allenol compound by intramolecular Prins cyclization in the presence of a Lewis acid:

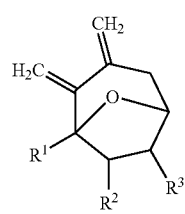
(I)

wherein $R^1$ is a hydrogen atom, $C_1$ to $C_6$ alkyl group or a phenyl group, and $R^2$ and $R^3$ is each a hydrogen atom, or $R^1$, $R^2$ and $R^3$ are connected with neighboring substituents to form a 5 to 10-membered aliphatic or aromatic ring.

18. The method of claim 17, wherein the reaction is conducted in a solvent selected from the group consisting of diethyl ether, tetrahydrofuran, dichloromethane and chloroform.

19. The method of claim 17, wherein said Lewis acid is trimethylsilyl trifluoromethanesulfonate (TMSOTf) and is used in an amount of 1.0 to 1.5 equivalent of said trimethylsilanylmethyl-allenol compound.

20. The method of claim 17, wherein the reaction is effected at a temperature in the range from −90° C. to 25° C.

21. The method of claim 17, wherein the reaction is effected at −78° C.

22. The method of claim 18, wherein the solvent is diethyl ether.

23. The method of claim 17, wherein the reaction is effected for 3 to 5 hours.

24. The method of claim 17, wherein the 7-membered carbocyclic compound is 1-methyl-2,3-dimethylene-8-oxa-bicyclo[3.2.1]octane.

25. The method of claim 17, herein the 7-membered carbocyclic compound is 2,3-dimethylene-1-phenyl-8-oxa-bicyclo[3.2.1]octane.

26. The method of claim 17, wherein the 7-membered carbocyclic compound is 9,10-dimethylene-12-oxa-tricyclo[6.3.1.0$^{2,7}$]dodeca-2,3,5-triene.

27. The method of claim 17, wherein the 7-membered carbocyclic compound is 9,10-dimethylene-11-oxa-tricyclo[5.3.1.0$^{1,5}$]undecane.

28. The method of claim 17, wherein the 7-membered carbocyclic compound is 10,11-dimethylene-12-oxa-tricyclo[6.3.1.0$^{1,6}$]dodecane.

29. The method of claim 17, wherein the 7-membered carbocyclic compound is 11,12-dimethylene-13-oxa-tricyclo[7.3.1.0$^{1,7}$]tridecane.

30. A method of preparing a 7-membered carbocyclic compound with diexomethylene groups, which comprises subjecting a trimethylsilanyl-allenol compound to an intramolecular Prins cyclization in the presence of a Lewis acid, to produce said 7-membered carbocyclic compound in a yield of at least 90%.

31. The method of claim 30, wherein the yield is 96%.

* * * * *